US012253528B2

(12) United States Patent
Cariou et al.

(10) Patent No.: US 12,253,528 B2
(45) Date of Patent: Mar. 18, 2025

(54) METHODS AND COMPOSITIONS FOR TREATING ASTHMA AND ALLERGIC DISEASES

(71) Applicants: INSERM (INSTITUT NATIONAL DE LA SANTÉ ET DE LA RECHERCHE MÉDICALE), Paris (FR); NANTES UNIVERSITE, Nantes (FR); CENTRE NATIONAL DE LA RECHERCHE SCIENTIFIQUE (CNRS), Paris (FR); INSTITUT NATIONAL DE RECHERCHE POUR L'AGRICULTURE, L'ALIMENTATION ET L'ENVIRONNEMENT, Paris (FR); CHU NANTES, Nantes (FR)

(72) Inventors: Bertrand Cariou, Nantes (FR); Antoine Magnan, Nantes (FR); Grégory Bouchaud, Nantes (FR); Cédric Le May, Nantes (FR)

(73) Assignees: INSERM (INSTITUT NATIONAL DE LA SANTE ET DE LA RECHERCHE MEDICALE), Paris (FR); UNIVERSITE DE NANTES, Nantes (FR); CENTRE NATIONAL DE LA RECHERCHE SCIENTIFIQUE (CNRS), Paris (FR); INSTITUT NATIONAL DE RECHERCHE POUR L'AGRICULTURE L'ALIMENTATION ET L'ENVRIONMENT, Paris (FR); CENTRE HOSPITALIER UNIVERSITAIRE DE NANTES, Nantes (FR)

( * ) Notice: Subject to any disclaimer, the term of this patent is extended or adjusted under 35 U.S.C. 154(b) by 980 days.

(21) Appl. No.: 17/273,082

(22) PCT Filed: Sep. 4, 2019

(86) PCT No.: PCT/EP2019/073546
§ 371 (c)(1),
(2) Date: Mar. 3, 2021

(87) PCT Pub. No.: WO2020/049026
PCT Pub. Date: Mar. 12, 2020

(65) Prior Publication Data
US 2021/0278420 A1 Sep. 9, 2021

(30) Foreign Application Priority Data
Sep. 5, 2018 (EP) .................... 18306169

(51) Int. Cl.
G01N 33/68 (2006.01)
A61P 37/08 (2006.01)
C07K 16/40 (2006.01)
C12N 15/113 (2010.01)

(52) U.S. Cl.
CPC .......... G01N 33/6893 (2013.01); A61P 37/08 (2018.01); C07K 16/40 (2013.01); C12N 15/1137 (2013.01); C07K 2317/76 (2013.01); C12N 2310/14 (2013.01); G01N 2333/96433 (2013.01); G01N 2800/122 (2013.01); G01N 2800/24 (2013.01); G01N 2800/56 (2013.01)

(58) Field of Classification Search
CPC ..... G01N 33/6893; G01N 2333/96433; G01N 2800/122; G01N 2800/24; G01N 2800/56; G01N 2333/956; A61P 37/08; A61P 11/06; C07K 16/40; C07K 2317/76; C12N 15/1137; C12N 2310/14; C12N 2310/11; C12N 2310/531; A61K 31/00
See application file for complete search history.

(56) References Cited

U.S. PATENT DOCUMENTS

2014/0162888 A1* 6/2014 Kuslich ................ C12Q 1/6886
506/9

FOREIGN PATENT DOCUMENTS

WO 2017/071673 A1 5/2017

OTHER PUBLICATIONS

Baldo, B.A. (2016). Other Approved Therapeutic Monoclonal Antibodies. In: Safety of Biologics Therapy. pp. 141-215. (Year: 2016).*
English translation of WO2017071673A1 Min et al. Application of PCSK9 inhibitor in preparation of drug trating inflammatory immune diseases. 2017. Genereated by Espacenet; no date for translation available. (Year: 2017).*
Valenta et al. Food allergies: The Basics. Gastroenterology, 2015, 148:1120-1131. (Year: 2015).*

(Continued)

Primary Examiner — Brad Duffy
Assistant Examiner — Amber K Faust
(74) Attorney, Agent, or Firm — WC&F IP

(57) ABSTRACT

The present invention relates to the allergy field. Several independent groups have recently investigated the implication of PCSK9 on inflammation and sepsis but none of them have determined its impact on allergies and/or asthma which is a global health burden. Inventors have obtained preliminary data on wild-type (PCSK9+/+) or PCSK9-deficient mice (PCSK9−/−) and shown that, under basal condition and in the absence of a particular stimulus, PCSK9 deficiency significantly increases the percentage of regulatory T cells in the spleen, the mesenteric lymph nodes and Peyer's patches. Moreover, inventors have shown the effect of allergic challenge on primary human bronchial epithelial cells on PCSK9 expression and secretion. Very interestingly, their first results obtained by Q-PCR showed that HDM and LPS increase PCSK9 mRNA levels. Accordingly, the present invention relates to inhibitors of PCSK9 for use in the treatment of asthma and/or allergic disease, such as food allergy.

11 Claims, 4 Drawing Sheets

(56) References Cited

OTHER PUBLICATIONS

Figure 1:
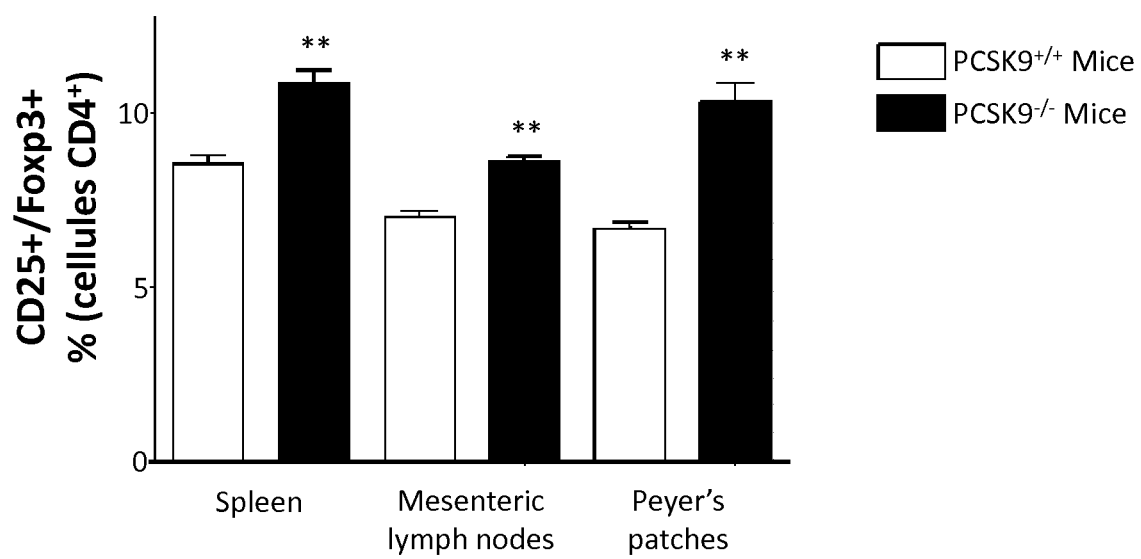

Berry et al: "Biomarkers in asthmatic patients: Has their time come to direct treatment?", Journal of Allergy and Clinical Immunology, vol. 137, No. 5, pp. 1317-1324, May 4, 2016.
Min et al: "In silico Screening of Chemical Libraries to Develop Inhibitors That Hamper the Interaction of PCSK9 with the LDL Receptor", Yonsei Medical Journal, vol. 56, No. 5, pp. 1251-1257, Jan. 1, 2015.
Sindher et al: "The Use of Biomarkers to Predict Aero-Allergen and Food Immunotherapy Response", Clinical Review in Allergy and Immunology, vol. 55, No. 2, pp. 190-204, Feb. 17, 2018.
Zhang et al: "Identification of a Small Peptide That Inhibits PCSK9 Protein Binding to the Low Density Lipoprotein Receptor" Journal of Biological Chemistry, vol. 289, No. 2, pp. 942-955, Nov. 13, 2013.

* cited by examiner

METHODS AND COMPOSITIONS FOR TREATING ASTHMA AND ALLERGIC DISEASES

FIELD OF THE INVENTION

The invention is in the field allergy. More particularly, the invention relates to methods and compositions to treat asthma and allergic diseases such as food allergy.

BACKGROUND OF THE INVENTION

PCSK9 (proprotein convertase subtilisin kexin type 9) is a critical regulator of cholesterol metabolism and PCSK9 inhibitors have been developed to treat hypercholesterolemia and cardiovascular diseases.

PCSK9 was discovered in 2003 in patients with autosomal dominant hypercholesterolemia (1) and quickly its canonical role as a natural inhibitor of the Low Density Lipoprotein Receptor (LDLR) has been established (2). After its autocleavage in the endoplasmic reticulum, PCSK9 is secreted as a mature form by the liver in the blood. PCSK9 binds to the extra-cellular domain of the LDLR and interferes with LDLR trafficking by promoting its lysosomal degradation rather than its recycling to the membrane. Genetic studies further established that PCSK9 deficiency is associated with reduced LDL-cholesterol (LDL-C) levels and a dramatic decrease of cardiovascular events (3), leading to the development of PCSK9 inhibitors. Recently, it has been shown that PCSK9 human monoclonal antibodies, that block the extra-cellular form of PCSK9, significantly reduced major cardiovascular events in hypercholesterolemic patients (4).

Beside this canonical role on hepatic LDLR pathway, numerous studies have shown that PCSK9 may exert some biological function on extra-hepatic organs (for review (5)). PCSK9 is abundantly expressed in the liver, but also in the gut, the kidneys, the lung and the thymus (6). PCSK9 is also secreted by the liver into the bloodstream and can act in an endocrine fashion to regulate LDLR expression in extra-hepatic tissues (7).

Beyond its role in lipid metabolism, some studies suggest that PCSK9 may also be involved in inflammatory responses. For instance, hepatic expression of PCSK9 is increased in response to lipopolysaccharide (LPS)-induced inflammation in mice (8). More recently, a link between PCSK9 and innate immune response and septic shock outcome has been highlighted by a series of independent studies (reviewed in (9)). PCSK9 deficiency or inhibition has been shown to be associated with an improved septic shock outcome in humans and mice, potentially due to an increased clearance of LPS in an LDLR-dependent manner (9). More recently, a study identified a link between hypercholesterolemia, PCSK9 overexpression and T cell-mediated inflammatory diseases (10). Mice overexpressing a PCSK9 "gain-of-function" mutant displayed a reduction of blood and spleen regulatory T cells and a concomitant increased of T Cells (CD3+/CD45+) in their lung. Histological analysis also revealed an increased perivascular and peribronchial inflammation in AAV8 PCSK9 treated mice (10).

Asthma is a common chronic respiratory disease that affects about 300 million people in the world. While asthma prevalence ranges from 1 to 16% of the population in different countries, the prevalence of food allergy is 3% and is constantly increasing. Among the various phenotypes of asthma, early-onset atopic Th2 type (11) is commonly associated with allergic disorders and appears to be the final stage of an "atopic march" from skin or intestinal inflammation leading to sensitization to aeroallergens, and progressing to bronchial asthma (12-14). This chronic inflammatory disease involves many players in immunity (IgE specific allergen, mast cells, cytokines) and organs (spleen, lymph nodes, intestine, lungs) whose functions can be quickly altered.

Several independent groups have recently investigated the implication of PCSK9 on sepsis but none of them have determined its impact on allergies and/or asthma which is a global health burden. Thus, there is a need to find new therapeutic strategies involved in immunity to treat asthma and food allergy.

SUMMARY OF THE INVENTION

The invention relates to an inhibitor of PCSK9 for use in the treatment of asthma and allergic diseases. In particular, the invention is defined by claims.

DETAILED DESCRIPTION OF THE INVENTION

Inventors have obtained preliminary data on wild-type (PCSK9+/+) or PCSK9-deficient mice (PCSK9-/-) and shown that, under basal condition and in the absence of a particular stimulus, PCSK9 deficiency significantly increases the percentage of regulatory T cells in the spleen, the mesenteric lymph nodes and Peyer's patches. Interestingly, the alteration of activation of these cells in allergy is considered as essential in the occurrence of chronic inflammation. Moreover, inventors have shown the effect of allergic challenge on primary human bronchial epithelial cells on PCSK9 expression and secretion. Very interestingly, their first results obtained by Q-PCR showed that House Dust Mite (HDM) allergens and LPS increase PCSK9 mRNA levels. Similarly, HDM induced a strong rise of intracellular PCSK9 protein content. They also observed a trend for intracellular PCSK9 increase when cells were cultured with LPS (+53%). They also found an increase of PCSK9 concentration in the media after HDM or LPS treatment.

Thus, inventors have found that PCSK9 could be a new potential therapeutic target to treat asthma and allergic diseases such as food allergy.

Method for Assessing or Predicting the Severity of Asthma or an Allerzic Disease Accordingly, the first object of the present invention relates a method for assessing or predicting the severity of asthma or the severity of an allergic disease in a subject, comprising i) determining the PCSK9 level in a biological sample obtained from the subject, ii) comparing the level determined at step i) with a predetermined reference value and iii) concluding that the subject has or is susceptible to have a severe asthma or severe allergic disease when the level of PCSK9 is higher than the predetermined reference value or concluding that the subject has not or is not susceptible to have a severe asthma or severe allergic disease when the level of PCSK9 is lower than the predetermined reference value.

In a particular embodiment, the method is suitable for predicting whether a subject is at risk of having asthma or severe asthma.

As used herein, the term "allergic diseases" or "allergies" refers to a reaction of immune system, particularly of specific IgE antibodies. Typically, the IgE antibodies and antigen bind to the membrane receptors of mast cells and granulocytes, the antigen-antibody reaction releases inflammatory mediators, vasodilation, capillary permeability hyperactivity, and cause such as tissue infiltration of inflammatory cells. Typically, the allergic disorder comprises allergic inflammation and/or chronic inflammation. For example, allergic disorder comprises allergic inflammation and is selected from allergic rhinitis, atopic dermatitis, allergic asthma, allergic conjunctivitis, gastro-intestinal inflammation, urticaria, and/or food allergy. In the context of the invention, the allergic disease is asthma, severe asthma or food allergy.

As used herein, the term "severity of asthma" refers to the Global Initiative for Asthma's (GINA) definition of severe asthma: asthma requiring high doses of inhaled steroids associated to another controller and/or oral steroids to be controlled, or uncontrolled despite such treatment.

As used herein, the term "risk" refers to the probability that an event will occur over a specific time period, such as the onset of severe asthma, and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed.

As used herein, the term "subject" refers to any mammals, such as a rodent, a feline, a canine, and a primate. Particularly, in the present invention, the subject is a human. In a particular embodiment, the subject is a human who suffers or is susceptible to have an asthma and/or allergic disease. More particularly, the subject has or is susceptible to have severe asthma or food allergy.

As used herein, the term "biological sample" refers to a sample obtained from a subject, for example blood, saliva, breast milk, urine, semen, blood plasma, synovial fluid, serum or plasma and bronchoalveolar lavage fluid (BAL). In a particular embodiment, the biological sample is blood sample. The term "blood sample" means any blood sample derived from the subject. Peripheral blood is preferred, and mononuclear cells (PBMCs) are the preferred cells. Typically, these cells can be extracted from whole blood using Ficoll, a hydrophilic polysaccharide that separates layers of blood, with the PBMC forming a cell ring under a layer of plasma. Additionally, PBMC can be extracted from whole blood using a hypotonic lysis which will preferentially lyse red blood cells. Such procedures are known to the expert in the art. In another embodiment, the biological sample is plasma and/or bronchoalveolar lavage fluid (BAL).

As used herein, the term "PCSK9" refers to proprotein convertase subtilisin/kexin type 9, also known as neural apoptosis-regulated convertase (NARC-1), is a proteinase K-like subtilase identified as the ninth member of the secretory subtilase family. PCSK9 is a natural inhibitor of LDL receptor (LDLR) and plays a critical role in cholesterol metabolism. PCSK9 binds the extracellular domain of LDLR and triggers its intracellular degradation, thereby controlling the levels of LDL particles that circulate in the bloodstream.

As used herein, the term "level" refers to the expression level of PCSK9. Typically, the expression level of the PCSK9 gene may be determined by any technology known by a person skilled in the art. In particular, each gene expression level may be measured at the genomic and/or nucleic and/or protein level. In a particular embodiment, the expression level of gene is determined by measuring the amount of nucleic acid transcripts of each gene. In another embodiment, the expression level is determined by measuring the amount of each gene corresponding protein. The amount of nucleic acid transcripts can be measured by any technology known by a man skilled in the art. In particular, the measure may be carried out directly on an extracted messenger RNA (mRNA) sample, or on retrotranscribed complementary DNA (cDNA) prepared from extracted mRNA by technologies well-known in the art. From the mRNA or cDNA sample, the amount of nucleic acid transcripts may be measured using any technology known by a man skilled in the art, including nucleic microarrays, quantitative PCR, microfluidic cards, and hybridization with a labelled probe. In a particular embodiment, the expression level is determined by using quantitative PCR. Quantitative, or real-time, PCR is a well-known and easily available technology for those skilled in the art and does not need a precise description. Methods for determining the quantity of mRNA are well known in the art. For example the nucleic acid contained in the biological sample is first extracted according to standard methods, for example using lytic enzymes or chemical solutions or extracted by nucleic-acid-binding resins following the manufacturer's instructions. The extracted mRNA is then detected by hybridization (e. g., Northern blot analysis) and/or amplification (e.g., RT-PCR). Preferably quantitative or semi-quantitative RT-PCR is preferred. Real-time quantitative or semi-quantitative RT-PCR is particularly advantageous. Other methods of amplification include ligase chain reaction (LCR), transcription-mediated amplification (TMA), strand displacement amplification (SDA) and nucleic acid sequence based amplification (NASBA). Nucleic acids having at least 10 nucleotides and exhibiting sequence complementarity or homology to the mRNA of interest herein find utility as hybridization probes or amplification primers. It is understood that such nucleic acids do not need to be identical, but are typically at least about 80% identical to the homologous region of comparable size, more preferably 85% identical and even more preferably 90-95% identical. In certain embodiments, it will be advantageous to use nucleic acids in combination with appropriate means, such as a detectable label, for detecting hybridization. A wide variety of appropriate indicators are known in the art including, fluorescent, radioactive, enzymatic or other ligands (e. g. avidin/biotin). Probes typically comprise single-stranded nucleic acids of between 10 to 1000 nucleotides in length, for instance of between 10 and 800, more preferably of between 15 and 700, typically of between 20 and 500. Primers typically are shorter single-stranded nucleic acids, of between 10 to 25 nucleotides in length, designed to perfectly or almost perfectly match a nucleic acid of interest, to be amplified. The probes and primers are "specific" to the nucleic acids they hybridize to, i.e. they preferably hybridize under high stringency hybridization conditions (corresponding to the highest melting temperature Tm, e.g., 50% formamide, 5× or 6×SCC. SCC is a 0.15 M NaCl, 0.015 M Na-citrate). The nucleic acid primers or probes used in the above amplification and detection method may be assembled as a kit. Such a kit includes consensus primers and molecular probes. A kit also includes the components necessary to determine if amplification has occurred. The kit may also include, for example, PCR buffers and enzymes; positive control sequences, reaction control primers; and instructions for amplifying and detecting the specific sequences. In a particular embodiment, the method of the invention comprises the steps of providing total RNAs extracted from a biological sample and subjecting the RNAs to amplification and hybridization to specific probes, more particularly by means of a quantitative or semi-quantitative RT-PCR. In another embodiment, the expression level is determined by DNA chip analysis. Such DNA chip or nucleic acid microarray consists of different nucleic acid probes that are chemically attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes comprise nucleic acids such as cDNAs or oligonucleotides that may be about 10 to about 60 base pairs. To determine the expression level, a biological sample from a test subject, optionally first subjected to a reverse transcription, is labelled and contacted with the microarray in hybridization conditions, leading to the formation of complexes between target nucleic acids that are complementary to probe sequences attached to the microarray surface. The labelled hybridized complexes are then detected and can be quantified or semi-quantified. Labelling may be achieved by various methods, e.g. by using radioactive or fluorescent labelling. Many variants of the microarray hybridization technology are available to the man skilled in the art (see e.g. the review by Hoheisel, Nature Reviews, Genetics, 2006, 7:200-210).

Mendelian randomization studies have been used to validate the relevance of PCSK9 inhibition for treating cardiovascular diseases. For instance, it has been demonstrated that for a 10 mg/dL reduction of LDL-cholesterol linked to loss-of-function variants in PCSK9, there was a 19% decrease in cardiovascular events (Ference B A, N Eng J Med, 2016; 375:2144-53).

Accordingly, in a particular embodiment, the detection of loss-of-function variants of PCSK9 can be performed in cohorts of patients with asthma or allergic diseases by the methods as described above. Typically, the detection of mutation R46L can be performed by the methods as described above. Mutation R46L is known to affect around 2% of the French population as found by the inventors in a previous study: Bonnefond A, Diabetologia, 2015, 58: 2051-5.

When a subject has a loss-of-function of PCSK9, it means that loss-of-function improves the allergic disease, more particularly the severity of the allergic disease is reduced.

In another embodiment, the measure of PCSK9 level is carried out by immunological detection. Typically, the immunological detection or quantification of the PCSK9 level is achieved by any methods known in the art using at least one antibody that binds specifically to PCSK9. Examples of said methods include, but are not limited to, standard electrophoretic and immunodiagnostic techniques such as western blots, immuno-precipitation assay, radioimmunoassay, ELISA (enzyme-linked immunosorbent assay), "sandwich" immunoassay, gel diffusion precipitation reaction, immunodiffusion assay, precipitation reaction, agglutination assay (such as gel agglutination assay, hemagglutination assay, etc.), complement fixation assay, protein A assay, immunoelectrophoresis assay, high performance liquid chromatography, size exclusion chromatography, solid-phase affinity, etc. In a particular embodiment, the level of PCSK9 is measured by ELISA. In a particular embodiment, the intracellular PCSK9 protein and secreted PCSK9 protein levels are measured.

As used herein, the term "predetermined reference value" refers to a threshold value or a cut-off value. Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. For example, retrospective measurement in properly banked historical subject samples may be used in establishing the predetermined reference value. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. For example, after determining the expression level of the selected peptide in a group of reference, one can use algorithmic analysis for the statistic treatment of the expression levels determined in samples to be tested, and thus obtain a classification standard having significance for sample classification. The full name of ROC curve is receiver operator characteristic curve, which is also known as receiver operation characteristic curve. It is mainly used for clinical biochemical diagnostic tests. ROC curve is a comprehensive indicator that reflects the continuous variables of true positive rate (sensitivity) and false positive rate (1-specificity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. The higher the area under the curve (AUC), the higher the accuracy of diagnosis. On the ROC curve, the point closest to the far upper left of the coordinate diagram is a critical point having both high sensitivity and high specificity values. The AUC value of the ROC curve is between 1.0 and 0.5. When AUC>0.5, the diagnostic result gets better and better as AUC approaches 1. When AUC is between 0.5 and 0.7, the accuracy is low. When AUC is between 0.7 and 0.9, the accuracy is moderate. When AUC is higher than 0.9, the accuracy is high. This algorithmic method is preferably done with a computer. Existing software or systems in the art may be used for the drawing of the ROC curve, such as: MedCalc 9.2.0.1 medical statistical software, SPSS 9.0, ROCPOWER.SAS, DESIGNROC.FOR, MULTIREADER POWER.SAS, CREATE-ROC.SAS, GB STAT VI0.0 (Dynamic Microsystems, Inc. Silver Spring, Md., USA), etc.

Method and Compositions for Treating Asthma and/or Allergic Diseases

The second object of the present invention relates to an inhibitor of PCSK9 for use in the treatment of asthma and/or allergic diseases in a subject in need thereof.

In particular, the invention relates to a method of treating asthma and/or allergic diseases in a subject in need thereof comprising a step of administering said subject with a therapeutically effective amount of a PCSK9 inhibitor.

In a particular embodiment, the inhibitor of PCSK9 for use according to the invention is suitable for treating asthma and/or severe asthma.

In another embodiment, the inhibitor of PCSK9 for use according to the invention suitable for treating allergic disease such as food allergy.

In a particular embodiment, the inhibitor of PCSK9 for use according to the invention, comprises the step of predicting whether the subject is at risk of having severe asthma or severe allergic diseases by performing the method of the invention.

As used herein, the term "treatment" or "treat" refer to both prophylactic or preventive treatment as well as curative or disease modifying treatment, including treatment of subjects at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

As used herein, the term "subject" refers to any mammals, such as a rodent, a feline, a canine, and a primate. Particularly, in the present invention, the subject is a human afflicted with or susceptible to be afflicted with at least one allergic disease. In a particular embodiment, the subject is a human afflicted with or susceptible to be afflicted with food allergy or asthma. In a particular embodiment, the subject suffers from food allergy. In a particular embodiment, the subject suffers from severe asthma.

As used herein, the term "allergic diseases" or "allergies" refers to a reaction of immune system, particularly of specific IgE antibodies. Typically, the IgE antibodies and antigen bind to the membrane receptors of mast cells and granulocytes, the antigen-antibody reaction releases inflammatory mediators, vasodilation, capillary permeability hyperactivity, and cause such as tissue infiltration of inflammatory cells. Typically, the allergic disorder comprises allergic inflammation and/or chronic inflammation. For example, allergic disorder comprises allergic inflammation and is selected from allergic rhinitis, atopic dermatitis, allergic asthma, allergic conjunctivitis, gastro-intestinal inflammation, urticaria, and/or food allergy.

As used herein, the term "food allergy" refers an adverse reaction to food mediated by an immunologic mechanism, involving specific IgE (IgE-mediated), cell-mediated mechanisms (non-IgE-mediated) or both IgE- and cell-mediated mechanisms (mixed IgE- and non-IgE-mediated). The organism fails to develop or a breakdown of food tolerance, resulting in excessive production of food-specific IgE antibodies or in altered cellular events, leading to allergic reactions. In particular, food allergy is implicated in Eosinophilic Esophagitis, Eosinophilic gastritis and gastroenteritis, food protein-induced enterocolitis syndrome, and allergic proctocolitis, Food-induced pulmonary haemosiderosis (Heiner's Syndrome), food-induced anaphylaxis (acute urticaria, anaphylactic shock and oedemas), and food-related atopic dermatitis and asthma.

As used herein, the term "asthma" refers to chronic respiratory disease and defines by World Health Organization (WHO) as a chronic disease characterized by recurrent attacks of breathlessness and wheezing, which vary in severity and frequency from person to person.

As used herein, the term "PCSK9" refers to proprotein convertase subtilisin/kexin type 9, also known as neural apoptosis-regulated convertase (NARC-1), is a proteinase K-like subtilase identified as the ninth member of the secretory subtilase family. PCSK9 is a natural inhibitor of LDL receptor (LDLR) and plays a critical role in cholesterol metabolism. PCSK9 binds the extracellular domain of LDLR and triggers its intracellular degradation, thereby controlling the levels of LDL particles that circulate in the bloodstream.

As used herein, the term "PCSK9 inhibitors" refers to a natural or synthetic compound that has a biological effect to inhibit or significantly reduce the activity or expression of PCSK9. It thus refers to any compound able to directly or indirectly decrease the transcription, translation, post-translational modification or activity of PCSK9. It includes intracellular as well as extracellular PCSK9 inhibitors.

In a particular embodiment, the inhibitor of PCSK9 activity for use in the invention is a small organic molecule, an aptamer, an antibody or a polypeptide.

As used herein the term "small organic molecule" refers to a molecule of a size comparable to those organic molecules generally used in pharmaceuticals. The term excludes biological macro molecules (e. g. proteins, nucleic acids, etc.). Typically, small organic molecules range in size up to about 5000 Da, more preferably up to 2000 Da, and most preferably up to about 1000 Da. In a particular embodiment, the small organic molecule is DS-9001a, comprising an albumin binding domain fused to an artificial lipocalin mutein (ABD-fused Anticalin protein). This small molecule is developed by Daiichi Sankyo/*Pieris* Pharmaceuticals (phase 1 ongoing).

As used herein the term "aptamers" refers to a class of molecule that represents an alternative to antibodies in term of molecular recognition. Aptamers are oligonucleotide or oligopeptide sequences with the capacity to recognize virtually any class of target molecules with high affinity and specificity.

As used herein the term "antibody" refers to any antibody-like molecule that has an antigen binding region, and this term includes antibody fragments that comprise an antigen binding domain such as Fab', Fab, F(ab')2, single domain antibodies (DABs or VHH), TandAbs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa(lamda) bodies (scFv-CL fusions); DVD-Ig (dual variable domain antibody, bispecific format); SIP (small immunoprotein, a kind of minibody); SMIP ("small modular immunopharmaceutical" scFv-Fc dimer; DART (ds-stabilized diabody "Dual Affinity ReTargeting"); small antibody mimetics comprising one or more CDRs and the like. The techniques for preparing and using various antibody-based constructs and fragments are well known in the art. Particularly, in the context of the invention, the antibody is a single domain antibody. The term "single domain antibody" has its general meaning in the art and refers to the single heavy chain variable domain of antibodies of the type that can be found in Camelid mammals which are naturally devoid of light chains. Such single domain antibody are also called VHH or "Nanobody®". For a general description of (single) domain antibodies, reference is also made to the prior art cited above, as well as to EP 0 368 684, Ward et al. (Nature 1989 Oct. 12; 341 (6242): 544-6), Holt et al., Trends Biotechnol., 2003, 21(11):484-490; and WO 06/030220, WO 06/003388. In the context of the invention, the amino acid residues of the single domain antibody are numbered according to the general numbering for VH domains given by the International ImMunoGeneTics information system amino acid numbering (www.imgt.org). Particularly, in the context of the invention, the antibody is a single chain variable fragment. The term "single chain variable fragment" or "scFv fragment" refers to a single folded polypeptide comprising the VH and VL domains of an antibody linked through a linker molecule. In such a scFv fragment, the VH and VL domains can be either in the VH-linker-VL or VL-linker-VH order. In addition to facilitate its production, a scFv fragment may contain a tag molecule linked to the scFv via a spacer. A scFv fragment thus comprises the VH and VL domains implicated into antigen recognizing but not the immunogenic constant domains of corresponding antibody. In a particular embodiment, the inhibitor of PCS9 activity is an intrabody having specificity for PCSK9. As used herein, the term "intrabody" generally refers to an intracellular antibody or antibody fragment. Antibodies, in particular single chain variable antibody fragments (scFv), can be modified for intracellular localization. Such modification may entail for example, the fusion to a stable intracellular protein, such as, e.g., maltose binding protein, or the addition of intracellular trafficking/localization peptide sequences, such as, e.g., the endoplasmic reticulum retention. In some embodiments, the intrabody is a single domain antibody.

In a particular embodiment, the inhibitor of PCSK9 activity for use in the invention is a monoclonal antibody.

In a particular embodiment, the inhibitor of PCSK9 for use in the invention is Evolocumab which is commercialized as Repatha® (or AMG 145) by Amgen and has the following formula in the art: $C_{6242}H_{9618}N_{1668}O_{1996}S_{56}$.

In a particular embodiment, the inhibitor of PCSK9 for use in the invention is Alirocumab which is commercialized as Praluent (REGN727 or SAR2365553) by Sanofi and Régéneron Pharmaceuticals and has the following formula in the art: $C_{6272}H_{9996}N_{1736}O_{2032}S_{42}$.

In a particular embodiment, the inhibitor of PCSK9 for use in the invention is Bococizumab also called as PF-04950615 or RN316 developed by PFIZER (phase 3 ongoing).

In a particular embodiment, the inhibitor of PCSK9 for use in the invention is LGT-209 developed by Novartis (phase 2 ongoing).

In a particular embodiment, the inhibitor of PCSK9 for use in the invention is RG-7652 developed by Roche (phase 2 ongoing).

In a particular embodiment, the inhibitor of PCSK9 for use in the invention is LY3015014 developed by Eli Lilly (phase 2 ongoing).

In a particular embodiment, the inhibitor of PCSK9 for use in the invention is MEDI 4166 developed by AstraZeneca and Medimmune. MEDI 4166 is a PCSK9 antibody fused to GLP1 peptide.

In a particular embodiment, the inhibitor of PCSK9 for use in the invention is AT04A or AT06A which is a vaccine developed by AFFiRiS AG (phase 1 ongoing), Landlinger C et al, Eur Heart J. 2017 Aug. 21.

As used herein, the term "polypeptide" refers to a polypeptide that specifically binds to PCSK9, can be used as a PCSK9 inhibitor that bind to sequester the PCSK9 protein, thereby preventing it from signaling. Polypeptide refers both short peptides with a length of at least two amino acid residues and at most 10 amino acid residues, oligopeptides (11-100 amino acid residues), and longer peptides (the usual interpretation of "polypeptide", i.e. more than 100 amino acid residues in length) as well as proteins (the functional entity comprising at least one peptide, oligopeptide, or polypeptide which may be chemically modified by being glycosylated, by being lipidated, or by comprising prosthetic groups). The definition of polypeptides also comprises native forms of peptides/proteins in mycobacteria as well as recombinant proteins or peptides in any type of expression vectors transforming any kind of host, and also chemically synthesized peptides. In a particular, the PCSK9 activity inhibitor is an intracellular peptide. Typically, intracellular peptide disturbs transmission of signals of PCSK9 mainly in the cytosol, mitochondria, and/or nucleus. In a particular embodiment, the polypeptide against PCSK9 activity is BMS-962476 as characterized by the amino acid sequences disclosed in WO 2011130354. This polypeptide is also described in Mitchell et al 2010 (J Pharmacol Exp Ther. 2014 August; 350(2):412-24. doi: 10.1124/jpet.114.214221. Epub 2014 Jun. 10.)

In a particular embodiment, the inhibitor of PCSK9 for use in the invention is an inhibitor of PCSK9 expression.

As used herein, the "inhibitor of PCSK9 expression" refers to a natural or synthetic compound that has a biological effect to inhibit or significantly reduce the expression of the gene encoding for PCSK9. Typically, the inhibitor of PCSK9 expression has a biological effect on one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

In some embodiments, the inhibitor of PCSK9 expression is an antisense oligonucleotide. Anti-sense oligonucleotides, including anti-sense RNA molecules and anti-sense DNA molecules, would act to directly block the translation of PCSK9 mRNA by binding thereto and thus preventing protein translation or increasing mRNA degradation, thus decreasing the level of PCSK9 proteins, and thus activity, in a cell. For example, antisense oligonucleotides of at least about 15 bases and complementary to unique regions of the mRNA transcript sequence encoding PCSK9 can be synthesized, e.g., by conventional phosphodiester techniques and administered by e.g., intravenous injection or infusion. Methods for using antisense techniques for specifically alleviating gene expression of genes whose sequence is known are well known in the art (e.g. see U.S. Pat. Nos. 6,566,135; 6,566,131; 6,365,354; 6,410,323; 6,107,091; 6,046,321; and 5,981,732).

In a particular embodiment, the inhibitor of PCSK9 expression is a shRNA. shRNA is generally expressed using a vector introduced into cells, wherein the vector utilizes the U6 promoter to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs that match the siRNA to which it is bound.

In some embodiments, the inhibitor of PCSK9 expression is a small inhibitory RNAs (siRNAs). PCSK9 expression can be reduced by contacting the subject or cell with a small double stranded RNA (dsRNA), or a vector or construct causing the production of a small double stranded RNA, such that PCSK9 expression is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836). In a particular embodiment, the siRNA is ALN-PCS02 also called as inclisiran developed by Alnylam (phase 3 ongoing), Ray K K et al, N Egnl J Med, April 2017.

In some embodiments, inhibitor of PCSK9 expression is a ribozyme. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of PCSK9 mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

In some embodiments, the inhibitor of PCSK9 expression is an endonuclease. The term "endonuclease" refers to enzymes that cleave the phosphodiester bond within a polynucleotide chain. Some, such as Deoxyribonuclease I, cut DNA relatively nonspecifically (without regard to sequence), while many, typically called restriction endonucleases or restriction enzymes, and cleave only at very specific nucleotide sequences. The mechanism behind endonuclease-based genome inactivating generally requires a first step of DNA single or double strand break, which can then trigger two distinct cellular mechanisms for DNA repair, which can be exploited for DNA inactivating: the errorprone nonhomologous end-joining (NHEJ) and the high-fidelity homology-directed repair (HDR).

In a particular embodiment, the endonuclease is CRISPR-cas. As used herein, the term "CRISPR-cas" has its general meaning in the art and refers to clustered regularly interspaced short palindromic repeats associated which are the segments of prokaryotic DNA containing short repetitions of base sequences. In some embodiment, the endonuclease is CRISPR-cas9 which is from *Streptococcus pyogenes*. The CRISPR/Cas9 system has been described in U.S. Pat. No. 8,697,359 B1 and US 2014/0068797. In some embodiment, the endonuclease is CRISPR-Cpf1 which is the more recently characterized CRISPR from *Provotella* and *Francisella* 1 (Cpf1) in Zetsche et al. ("Cpf1 is a Single RNA-guided Endonuclease of a Class 2 CRISPR-Cas System (2015); Cell; 163, 1-13).

As used herein the terms "administering" or "administration" refer to the act of injecting or otherwise physically delivering a substance as it exists outside the body (e.g., an inhibitor of PCSK9) into the subject, such as by mucosal, intradermal, intravenous, subcutaneous, intramuscular delivery and/or any other method of physical delivery described herein or known in the art. When a disease, or a symptom thereof, is being treated, administration of the substance typically occurs after the onset of the disease or symptoms thereof. When a disease or symptoms thereof, are being prevented, administration of the substance typically occurs before the onset of the disease or symptoms thereof.

As used herein, the term "therapeutically effective amount" refers to a sufficient amount of PCSK9 inhibitors to treat the disease (e.g. food allergy and/or asthma) at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular patient will depend upon a variety of factors including the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, typically from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The PCSK9 inhibitors as described above may be administered in combination with a classical treatment of asthma or allergic disease.

Thus, the invention relates to a i) a PCSK9 inhibitor and ii) a classical treatment as a combined preparation for use in the treatment a subject suffering from asthma or allergic disease.

As used herein, the term "classical treatment" refers to any refers to any compound, natural or synthetic, used for the treatment of asthma or allergic disease.

In a particular embodiment, the classical treatment of asthma or allergic disease refers to β-adrenoceptor agonist such as corticosteroids such as flunisolide, ciclesonide, mometasone, fluticasone, budesonide, beclomethasone and prednisome; bronchodilators such as epinephrine, racepinephrine, indacaterol, albuterol, levalbuterol, olodaterol, formoterol, arformoterol, pirbuterol, terbutaline, metaproterenol, salmeterol, ipratropium, aclidinium, tiotropium, umeclidinium, glycopyrrolate and revefenacin; methylxanthines such as theophylline, dyphylline, and aminophylline; anti-leukotriene drugs such as montelukast, zafirkulast and zileuton; interleukin inhibitors such as reslizumab, dupilumab, benralizumab, mepolizumab and omalizumab; mast cell stabilizer such as cromolyn; allergen immunotherapy such as grastek, oralair and ragwitek.

As used herein, the terms "combined treatment", "combined preparation", "combined therapy" or "therapy combination" refer to a treatment that uses more than one medication. The combined therapy may be dual therapy or bi-therapy.

The medications used in the combined treatment according to the invention are administered to the subject simultaneously, separately or sequentially.

As used herein, the term "administration simultaneously" refers to administration of 2 active ingredients by the same route and at the same time or at substantially the same time. The term "administration separately" refers to an administration of 2 active ingredients at the same time or at substantially the same time by different routes. The term "administration sequentially" refers to an administration of 2 active ingredients at different times, the administration route being identical or different The PCSK9 inhibitors as described above may be combined with pharmaceutically acceptable excipients, and optionally sustained-release matrices, such as biodegradable polymers, to form pharmaceutical compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. The pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The polypeptide (or nucleic acid encoding thereof) can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

Method of Screening

In a third aspect, the invention relates to a method of screening a drug suitable for inhibiting PCSK9 comprising i) providing a test compound and ii) determining the ability of said test compound to inhibit the expression or activity of PCSK9.

Any biological assay well known in the art could be suitable for determining the ability of the test compound to inhibit the activity or expression of PCSK9. In some embodiments, the assay first comprises determining the ability of the test compound to bind to PCSK9. In some embodiments, a population cell is then contacted and activated so as to determine the ability of the test compound to inhibit the activity or expression of PCSk9. In particular, the effect triggered by the test compound is determined relative to that of a population of cells incubated in parallel in the absence of the test compound or in the presence of a control agent either of which is analogous to a negative control condition. The term "control substance", "control agent", or "control compound" as used herein refers a molecule that is inert or has no activity relating to an ability to modulate a biological activity or expression. It is to be understood that test compounds capable of inhibiting the activity or expression of PCSK9, as determined using in vitro methods described herein, are likely to exhibit similar modulatory capacity in applications in vivo. Typically, the test compound is selected from the group consisting of peptides, petptidomimetics, small organic molecules, antibodies (e.g. intra-antibodies), aptamers or nucleic acids. For example the test compound according to the invention may be selected from a library of compounds previously synthesised, or a library of compounds for which the structure is determined in a database, or from a library of compounds that have been synthesised de novo.

The invention will be further illustrated by the following figures and examples. However, these examples and figures should not be interpreted in any way as limiting the scope of the present invention.

FIGURES

FIG. 1. Regulatory T cells are significantly more abundant in the spleen, mesenteric lymph nodes and Peyer's patches of PCSK9−/− mice.

Figures 2A, 2B, 2C:
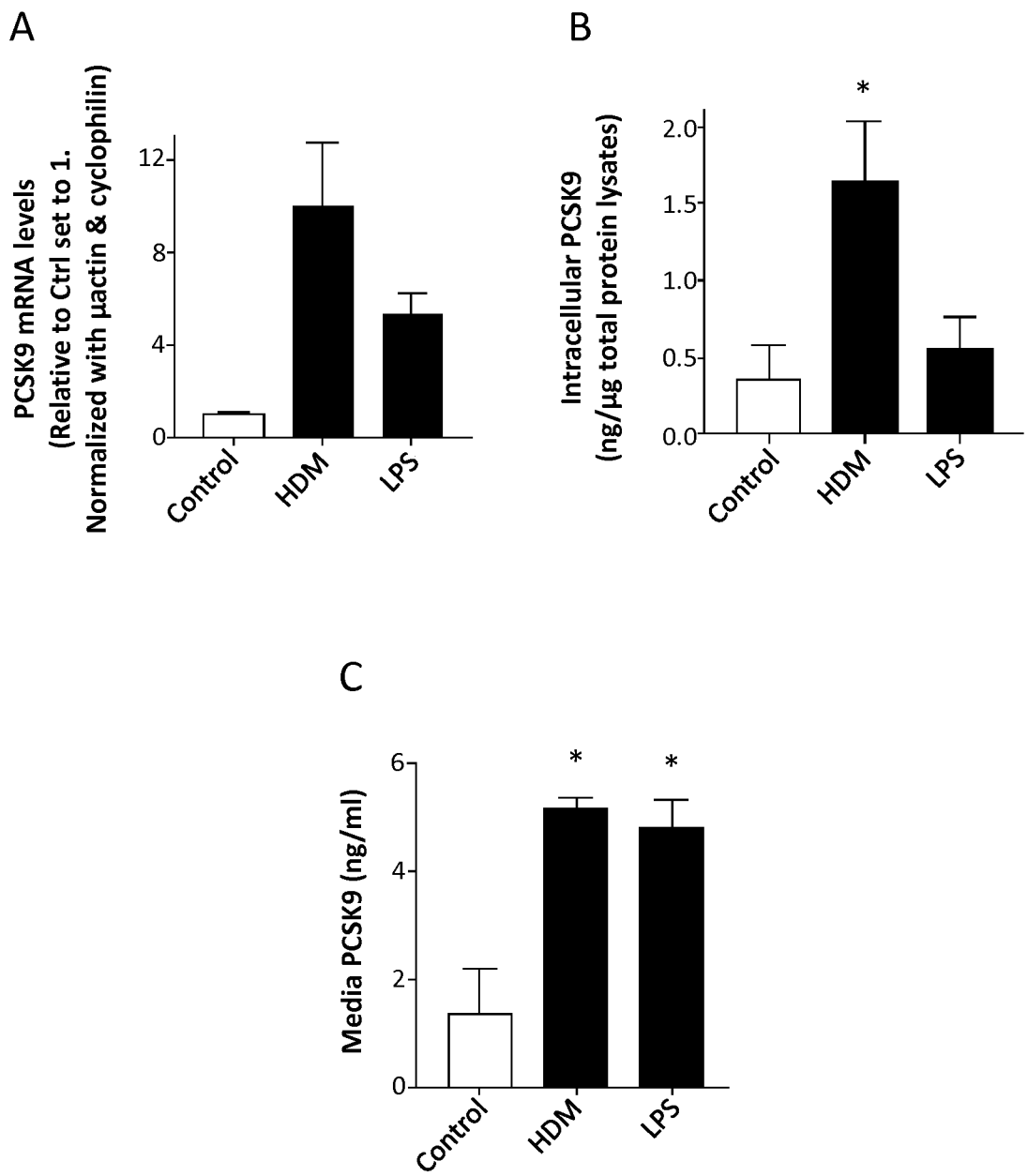

FIG. 2. HDM allergens increase the intracellular PCSK9 expression and possibly its secretion. Human primary BECs were cultured for 48 hours with HDM allergens or LPS (10 µg/ml). (A) PCSK9 mRNA levels (B) Intracellular PCSK9 protein and (C) "secreted" PCSK9 protein levels. Protein levels were assayed by ELISA. *P<0.05.

FIG. 3. PCSK9 deficiency attenuates the allergic responses. PCSK9+/+(white circle) and PCSK9−/− mice (black circle) were sensitized by intra-peritoneal injection of vehicle (white bars) or gliadins (black bars) and then challenged twice with water or gliadins by gavage. One hour after the second oral allergic challenge body weight (A), plasma PCSK9 concentrations (B) ear thickness (C) were measured and represented as dot plots and histograms representing mean±SEM. One hour after the second oral allergic challenge spleen weight (D), splenic CD19+ IgE+ cells percentage (E) and plasma gliadin specific IgE concentrations (F) were measured and represented as dot plots and bars representing mean±SEM. Statistical significance was analyzed using non-parametric Mann-Whitney test with Graphprism® (Graphpad Software). *P<0.05; P<0.01; *P<0,001; ****P<0,0001; NS: Non Significant.

EXAMPLE

Our laboratory has access to human primary bronchial epithelial cells (Human primary BECs) via the multicentre Cohort of Lung Transplantation (COLT—NCT00980967 study/CPP 2009—A00036-51). Briefly, these cells are dissociated from lung donor trachea or bronchi via overnight incubation at 4° C. with type XIV collagenase in HEPES-buffered RPMI. Humans BECs are then cultured in cnT17 media containing penicillin and streptomycin on human type IV collagen coated plates (19). Considering the PCSK9 expression in the gut and the lung and its potential role in immunity, we hypothesize that PCSK9 may play a role in both food allergy and progression towards respiratory pathological complications such as asthma. Preliminary data obtained in our laboratory on wild-type (PCSK9+/+) or PCSK9-deficient mice (PCSK9−/−) show that, under basal condition and in the absence of a particular stimulus, PCSK9 deficiency significantly increases the percentage of regulatory T cells in the spleen, the mesenteric lymph nodes and Peyer's patches (FIG. 1). Interestingly, the alteration of activation of these cells in allergy is considered as essential in the occurrence of chronic inflammation. Our driving hypothesis is that PCSK9 deficiency protects against food allergy & asthma.

Very interestingly, our first results obtained by Q-PCR showed that HDM and LPS increase PCSK9 mRNA levels. Similarly, HDM induced a strong rise of intracellular PCSK9 protein content. We also observed a non-significant trend for intracellular PCSK9 increase when cells were cultured with LPS (+53%). We also found an increase of PCSK9 concentration in the media after HDM or LPS treatment (FIG. 2). These first results are reassuring about the relevance of the use of this cell model and suggest that PCSK9 is expressed in bronchial epithelial cells and regulated during inflammatory process.

Figures 3A, 3B, 3C:
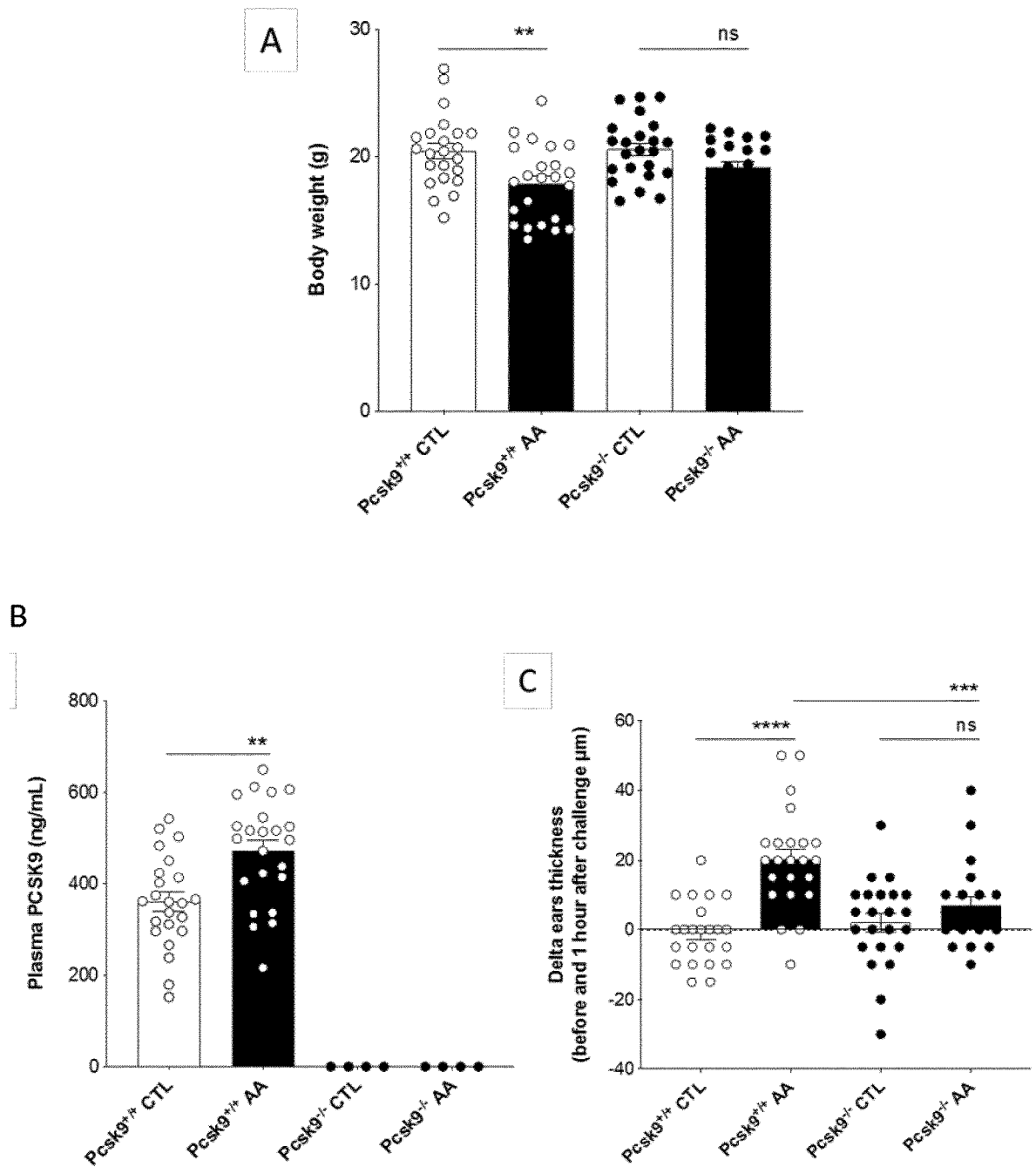
Figures 3D, 3E, 3F:
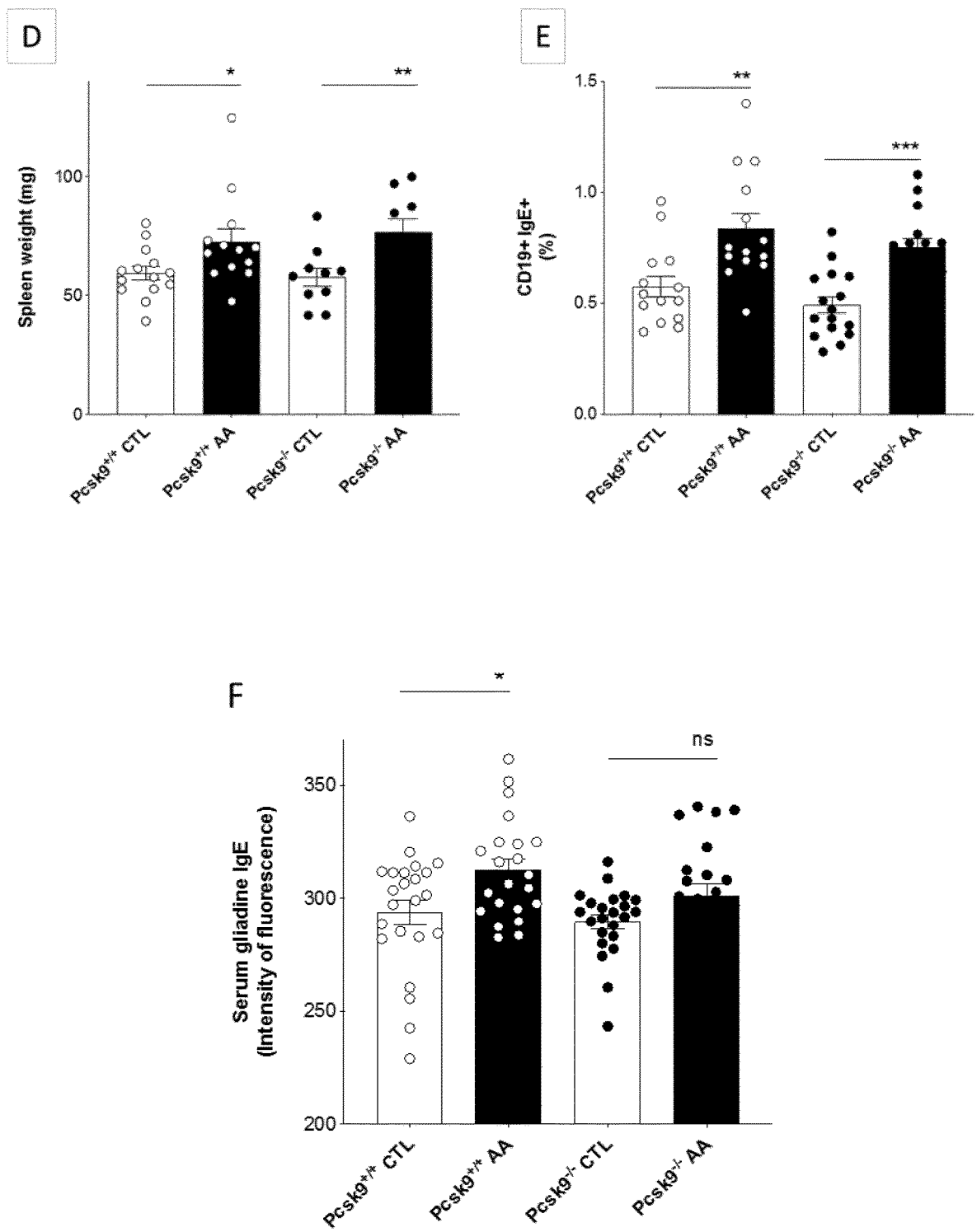

Then an allergy induction was proceeded. The allergy induction protocols were set up routinely at l'Institut du Thorax and were previously described in detail (17). We used PCSK9+/+ and PCSK9−/− males and females mice fed since weaning with gluten free regular chow diet. In order to induce sensitization, 5 weeks old mice received 3 consecutive intraperitoneal injection with either vehicle or deamidated wheat gliadins (10 micrograms) on days 0, 10 and 20. Mice were then challenged twice by oral administration of 20 milligrams of deamidated gliadins. Results shown on figure 3 & 4 were obtained 1 h after the second allergic challenge. We did observe that PCSK9$^{+/+}$ mice under allergic condition (Alimentary Allergy, AA) have a reduced body weight compared to control PCSK9$^{+/+}$ mice (FIG. 3A). We also observed a slight trend for body weight decrease in PCSK9$^{-/-}$ under allergic condition however it did not reach significancy (FIG. 3A). Interestingly, plasma PCSK9 levels are significantly increased after allergy induction in PCSK9$^{+/+}$ mice (FIG. 3B). Gliadin challenge increased spleen weight (FIG. 3D) and IgE+ plasmocytes % (FIG. 3E) in both PCSK9$^{+/+}$ and PCSK9$^{-/-}$ mice. By contrast, the plasma gliadin specific IgE+ concentrations is significantly increased in allergy PCSK9$^{+/+}$ mice but not in PCSK9$^{-/-}$ mice (FIG. 3F) suggesting that PCSK9 deficiency attenuates the allergic responses. To characterize the allergic symptoms, we measured ear thickness with a micrometer after the oral challenge. In control groups, the vehicle solution gavage did not affect ear thickness in both PCSK9$^{+/+}$ and PCSK9$^{-/-}$ mice. We show a significant increase in ear thickness after the oral challenge for the PCSK9$^{+/+}$ mice sensitized and challenged with the deamidated form of gliadins (FIG. 3C). By contrast, no effect was observed in PCSK9$^{-/-}$ mice in the same condition (FIG. 3C).

REFERENCES

Throughout this application, various references describe the state of the art to which this invention pertains. The disclosures of these references are hereby incorporated by reference into the present disclosure.

1) Abifadel M. et al. Mutations in PCSK9 cause autosomal dominant hypercholesterolemia. Nat Genet 2003; 34: 154-6.
2) Seidah N G et al. PCSK9: a key modulator of cardiovascular health. Circ Res 2014; 114: 1022-36.
3) Cohen J C et al. Sequence variations in PCSK9, low LDL, and protection against coronary heart disease. N Engl J Med. 2006; 354:1264-72.
4) Sabatine M. S. et al. Evolocumab and Clinical Outcomes in Patients with Cardiovascular Disease. N Engl J Med. 2017; 376:1713-1722.
5) Cariou B et al. Role of PCSK9 beyond liver involvement. Curr Opin Lipidol. 2015 June; 26(3):155-6
6) Seidah N. G. et al. The secretory proprotein convertase neural apoptosis-regulated convertase 1 (NARC-1): liver regeneration and neuronal differentiation. Proc Natl Acad Sci USA. 2003; 100:928-33.
7) Lagace T. A. et al. Secreted PCSK9 decreases the number of LDL receptors in hepatocytes and in livers of parabiotic mice. J Clin Invest. 2006; 116: 2995-3005.
8) Feingold K. R. et al. Inflammation stimulates the expression of PCSK9. Biochem Biophys Res Commun. 2008; 374: 341-4.
9) Khademi F. et al. PCSK9 and infection: A potentially useful or dangerous association? J Cell Physiol. 2017 June; 1-8.
10) Proto J. D. et al. Hypercholesterolemia induces T cell expansion in humanized immune mice. J Clin Invest. 2018 Apr. 30. pii: 97785. doi: 10.1172/JC197785.
11) Haldar P. et al. Cluster analysis and clinical asthma phenotypes. Am J Respir Crit Care Med 2008, 178:218-224.
12) Dharmage S. C. et al. Atopic dermatitis and the atopic march revisited. Allergy 2014, 69:17-27.
13) Lin Y. T. et al. Correlation of ovalbumin of egg white components with allergic diseases in children. J Microbiol Immunol Infect 2016; 49:112-8.
14) Bieber T. et al. Atopic dermatitis: a candidate for disease-modifying strategy. Allergy 2012, 67:969-975.
15) Bihouée T. et al. Food allergy enhances allergic asthma in mice. Respir Res. 2014; 15:142.
16) Bouchaud G. et al. Consecutive Food and Respiratory Allergies Amplify Systemic and Gut but Not Lung Outcomes in Mice. J Agric Food Chem. 2015; 63: 6475-83.
17) Bouchaud G. et al. Maternal exposure to GOS/inulin mixture prevents food allergies and promotes tolerance in offspring in mice. Allergy. 2016; 71: 68-76.
18) Castan L. et al. Food allergen-sensitized CCR9+ lymphocytes enhance airways allergic inflammation in mice. Allergy. 2018 Jan. 9. doi: 10.1111/all.13386.
19) Pain M. et al. T Cells Promote Bronchial Epithelial Cell Secretion of Matrix Metalloproteinase-9 via a C—C Chemokine Receptor Type 2 Pathway: Implications for Chronic Lung Allograft Dysfunction. Am J Transplant. 2017; 17: 1502-1514.
20) Rusznak C. et al. Cigarette smoke potentiates house dust mite allergen-induced increase in the permeability of human bronchial epithelial cells in vitro. Am J Respir Cell Mol Biol. 1999 June; 20(6):1238-50.
21) Zaid A. et al. Proprotein convertase subtilisin/kexin type 9 (PCSK9): hepatocyte-specific low-density lipoprotein receptor degradation and critical role in mouse liver regeneration. Hepatology. 2008 August; 48(2):646-54.
22) Bonnefond A. et al. The loss-of-function PCSK9 p.R46L genetic variant does not alter glucose homeostasis. Diabetologia. 2015 September; 58(9):2051-5.
23) Weider E. et al. Proprotein Convertase Subtilisin/Kexin Type 9 (PCSK9) Single Domain Antibodies Are Potent Inhibitors of Low Density Lipoprotein Receptor Degradation. J Biol Chem. 2016 Aug. 5; 291(32):16659-71.
24) Sutherland S. D. et al. Cell of Origin of Small Cell Lung Cancer: Inactivation of Trp53 and Rb1 in Distinct Cell Types of Adult Mouse Lung. Cancer Cell, Jun. 14, 2011: 19, 754-764.

The invention claimed is:

1. A method for assessing or predicting severity of an allergic disease in a subject, comprising
   i) determining a PCSK9 level in a biological sample obtained from the subject,
   ii) comparing the level determined at step i) with a predetermined reference value,
   iii) concluding that the subject has or is susceptible to have a severe allergic disease when the level of PCSK9 is higher than the predetermined reference value, wherein the allergic disease is selected from the group consisting of a food allergy, allergic rhinitis and asthma, and
   iv) administering to the subject a therapeutically effective amount of a pharmaceutical composition comprising a PCSK9 inhibitor.

2. The method according to claim 1 wherein the biological sample is a blood sample and/or a bronchoscopy and bronchoalveolar lavage (BAL) sample.

3. The method of claim 1 wherein the biological sample is a peripheral blood mononuclear cell (PBMC) sample.

4. The method according to claim 1 wherein the PCSK9 level is measured by ELISA.

5. The method of claim 1, wherein the inhibitor of PCSK9 is selected from the group consisting of alirocumab, evolocumab and bococizumab.

6. A method of treating allergic disease in a subject in need thereof comprising administering to the subject a therapeutically effective amount of an inhibitor of PCSK9, wherein the allergic disease is asthma or food allergy, and wherein the method comprises predicting whether the subject is at risk of having the allergic disease by
   i) determining the PCSK9 level in a biological sample obtained from the subject,
   ii) comparing the level determined at step i) with a predetermined reference value
   iii) concluding that the subject has or is susceptible to have severe allergic disease when the level of PCSK9 is higher than the predetermined reference value, and
   iv) administering the therapeutically effective amount of the inhibitor of PCSK9.

7. The method according to claim 6, wherein the inhibitor is an antibody.

8. The method according to claim 6, wherein the inhibitor is alirocumab, evolocumab or bococizumab.

9. A method of treating or inhibiting severe asthma or food allergy in a subject in need thereof, comprising
   i) measuring a PCSK9 level in a biological sample obtained from the subject,
   ii) comparing the level determined at step i) with a predetermined reference value
   iii) determining that the subject has or is susceptible to have severe asthma or food allergy when the level of PCSK9 is higher than the predetermined reference value, and
   iv) administering to the subject a therapeutically effective amount of a pharmaceutical composition comprising an inhibitor of PCSK9 selected from the group consisting of alirocumab, evolocumab and bococizumab.

10. The method of claim 9, wherein the pharmaceutical composition further comprises at least one β-adrenoceptor agonist selected from the group consisting of a corticosteroid, a bronchodilator, a methylxanthine, an anti-leukotriene, an interleukin inhibitor a mast cell stabilizer and an allergen immunotherapy.

11. The method according to claim 6, wherein the allergic disease is a food allergy.

\* \* \* \* \*